Figure 1:
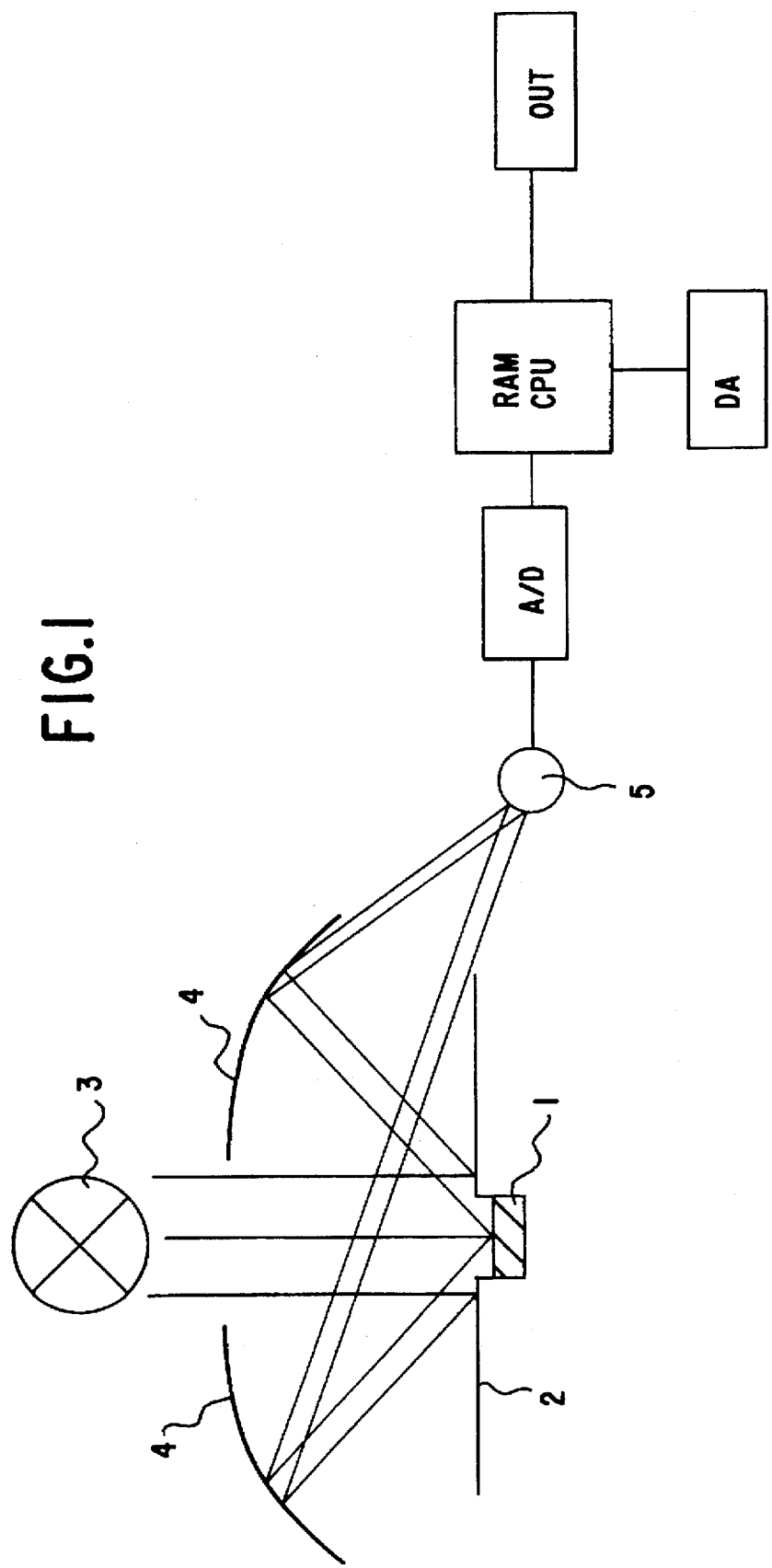

United States Patent [19]

Backhaus et al.

[11] Patent Number: 5,734,587
[45] Date of Patent: Mar. 31, 1998

[54] METHOD OF ANALYZING CLINICALLY RELEVANT LIQUIDS AND SUSPENSIONS

[75] Inventors: Juergen Backhaus, Edingen-Neckarhausen; Dirk Boecker, Heidelberg; Reinhard Mischler, Ludwigshafen, all of Germany

[73] Assignee: Boehringer Mannheim GmbH, Mannheim, Germany

[21] Appl. No.: 307,416

[22] Filed: Sep. 19, 1994

[30] Foreign Application Priority Data

Sep. 17, 1993 [DE] Germany ................ 43 31 596.8
Apr. 30, 1994 [DE] Germany ................ 44 15 253.1

[51] Int. Cl.$^6$ ................................................ G01N 21/01
[52] U.S. Cl. .................. 364/498; 436/46; 436/50; 282/133; 282/161
[58] Field of Search ................ 364/496–499, 364/413.07–413.11; 436/46, 50, 63; 382/133, 134, 155–161; 356/36–42, 51

[56] References Cited

U.S. PATENT DOCUMENTS

| | | | |
|---|---|---|---|
| 4,017,192 | 4/1977 | Rosenthal | 356/432 |
| 4,975,581 | 12/1990 | Robinson et al. | 364/498 |
| 5,121,337 | 6/1992 | Brown | 364/498 |
| 5,121,338 | 6/1992 | Lodder | 364/498 |
| 5,124,932 | 6/1992 | Lodder | 364/498 |
| 5,290,705 | 3/1994 | Davis | 436/164 |
| 5,334,837 | 8/1994 | Ikeda et al. | 250/339.11 |
| 5,435,309 | 7/1995 | Thomas et al. | 128/633 |

FOREIGN PATENT DOCUMENTS

| | | |
|---|---|---|
| 0 419 222A2 | 3/1991 | European Pat. Off. . |
| 4-283651 | 8/1992 | European Pat. Off. . |
| 0 457 789B1 | 11/1992 | European Pat. Off. . |
| 0 456 695B1 | 1/1993 | European Pat. Off. . |
| 32 47 891A1 | 6/1984 | Germany . |
| 1-196539 | 8/1989 | Japan . |
| 1-239631 | 9/1989 | Japan . |
| 3-113351 | 5/1991 | Japan . |
| 3-262944 | 11/1991 | Japan . |
| 4-151545 | 5/1992 | Japan . |
| 5-99813 | 4/1993 | Japan . |
| 7-500180 | 1/1995 | Japan . |
| WO93/00580 | 1/1993 | WIPO . |

OTHER PUBLICATIONS

*Journal of The American Statistical Association*, vol. 84, No. 405, Mar. 1989.
*Patent Abstracts of Japan*, vol. 17, No. 82, Feb. 18, 1993.
*Patent Abstracts of Japan*, vol. 12, No. 492, Nov. 8, 1989.
*Applied Spectroscopy*, vol. 47, No. 9, pp. 1519–1521.
International Publication No. WO 90/15981 published Dec. 27, 1990.

Primary Examiner—Emanuel T. Voeltz
Assistant Examiner—Kyle J. Choi
Attorney, Agent, or Firm—Nikaido, Marmelstein, Murray & Oram LLP

[57] ABSTRACT

A method of analyzing clinically relevant sample liquids and suspensions is such that where infrared spectra of dried samples are generated and evaluated using a multivariate evaluation procedure. In the evaluation procedure, the samples to be analyzed are assigned to classes. The evaluation procedure is trained with samples of known classes to adjust the parameters of the evaluation procedures such that samples of unknown classification can be assigned to known classes. In an advantageous manner, the infrared spectra can be generated by a transmittance measurement on a dried film of the sample.

27 Claims, 10 Drawing Sheets

FIG.2
CALIBRATION (TRAINING)
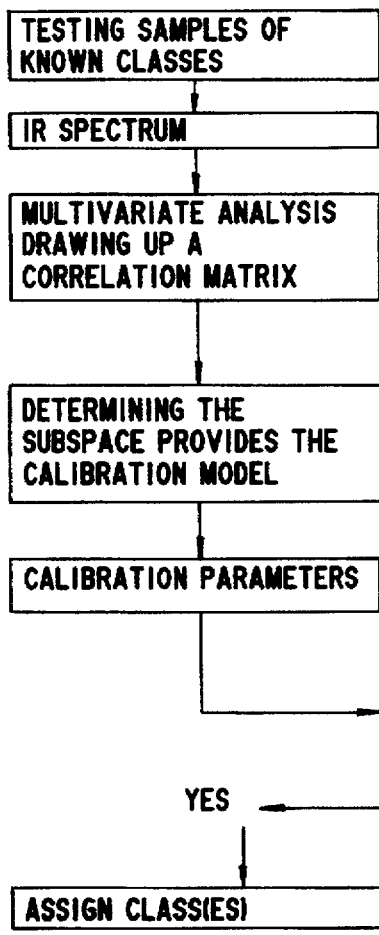
MEASURING UNKNOWN SAMPLES
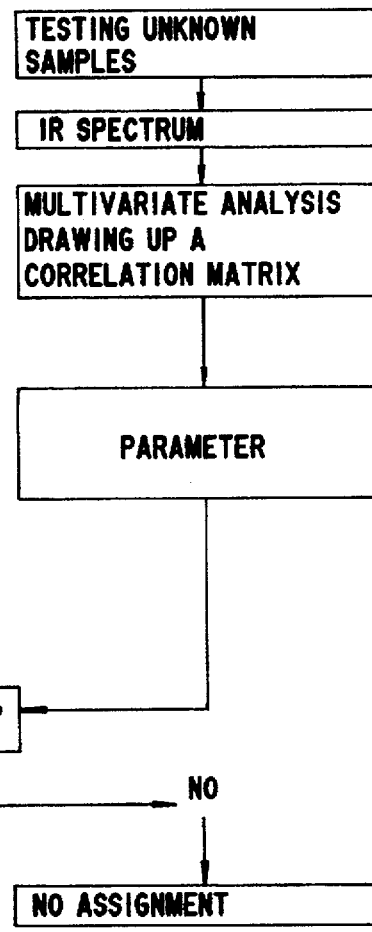

METHOD OF ANALYZING CLINICALLY RELEVANT LIQUIDS AND SUSPENSIONS

The present invention relates to a method of analyzing and classifying clinically relevant liquids and suspensions by using a multivariate evaluation procedure with class assignment. In the procedure, a sample is applied to a carrier, an infrared spectrum of the dried sample is generated, the infrared spectrum is evaluated using the multivariate evaluation procedure, and the sample is assigned to a class. The present invention also relates to carrier for carrying out transmittance measurements with samples.

In the prior art, Alfa Laval and Bruker describe methods where food or objects of daily needs are analyzed by means of infrared spectroscopy and results are subject to discriminant analysis. However, with respect to sample collection and sample preparation, these methods greatly differ from evaluation procedures known in clinical chemistry. Moreover, samples that are analyzed by methods known in the analysis of food also differ from the sample material used in clinical chemistry, especially with respect to the typical deviation range of the properties to be analyzed. In clinical chemistry, these are usually so low that the spectroscopic reproducibility must fulfill considerably higher demands. Based on the difference among the sample materials used, the methods described in the prior art could not be applied to the field of the invention.

Eysel et al. describe a method of analyzing knee-joint liquid and indicate that all data were evaluated with modern statistical methods. In this procedure which is described in Applied Spectroscopy 47, pages 1519–1521 (1993), knee-joint liquid was transferred into a calcium chloride measuring cell and an infrared spectrum was measured. This publication also describes the IR spectrum of a quantity of dried knee-joint liquid. Based on a comparison of the two spectra, the authors conclude that the individual absorption bands that carbon dioxide clathrate is present in the water-containing knee-joint liquid. The presence of these clathrates is connected with the occurrence of arthritis. The basis for this method is the evaluation of radiation that has passed through the sample. To accomplish this, the sample must be applied onto a calcium fluoride disk. The high price of calcium fluoride carders, however, does not bode well for the implementation of a single use technology. Accordingly, the use of calcium fluoride carriers requires complex cleaning steps. Experience has also shown that when more complex samples, e.g. blood serum, are used the described method does not produce sufficiently reproducible results.

It was, hence, object of the present invention to provide a method whereby sample liquids and/or suspensions can be clearly and reliably associated with clinically relevant classes. The object was, hence, to find a method which exhibits a high reproducibility and allows analyzing even complex body liquids, as well as cell/bacteria suspensions in a simple and inexpensive manner.

It was another object of the invention to provide a method of analyzing sample liquids and/or suspensions where the classification does not require the addition of reagents. It was a particular object of the invention to simplify the analysis and classification of these samples.

A method for analyzing clinically relevant liquids and suspensions was found which comprises the following steps:

measuring infrared spectra of a plurality of samples which belong to known classes, implementing a multivariate evaluation procedure while minimizing misassignments between samples and known classes, storing the parameters of the multivariate evaluation procedures which were obtained by minimization, providing a sample of the liquid and/or suspension, applying the sample to a carrier, drying the sample, exposing the sample to infrared radiation, generating an infrared spectrum of the sample, analyzing the infrared spectrum by means of a multivariate evaluation procedure, assigning the sample to a class of the multivariate evaluation procedure.

Methods in accordance with the invention address the analysis of body fluids, and cell/bacteria suspensions. Clinically relevant body fluids which can be analyzed with this method include blood, plasma, serum, hemolysate, urine, liquor, saliva, perspiration liquid, vitreous humor, cystic fluid, amniotic liquid, sputum, ascitis, and spermatic fluid. Cell/bacteria suspensions are those samples which can be obtained either directly (by means of puncturing or smears) or by growing in a culture medium.

The method of the invention is particularly suited to analyze liquids which contain a great variety of different substances. In particular, these are blood, plasma, serum, and hemolysate.

The complete contents of German Patent Application P 43 31596.8 is included in this application by reference.

When the method of the invention is carried out, the first step is to make available the sample liquid and/or suspension to be classified. This can be done in a well-known manner, e.g. by collecting blood or urine specimens. With some kinds of samples, it is advantageous to pretreat the samples prior to beginning the procedure. Whole blood, for example, can be centrifuged to separate serum and blood clots.

The so-obtained sample is placed onto a carrier which allows generating an infrared spectrum. Such a carrier can, for example, be a metalized microscopic slide. Preferred carrier are those with a reflecting surface and a roughness which provokes a diffuse diffraction of the infrared radiation. It is also possible to use carriers where the surface onto which the samples are applied reflects the radiation. The carriers can be coated with metals, preferably noble metals, such as gold, platinum, palladium; but inoble metals, preferably aluminum and chromium are also possible. The advantage of these coatings is that they are largely inert with respect to both samples and ambient air. The carriers can have an even surface onto which the sample is applied. In accordance with the invention, preferred carriers have a recess to receive the sample liquid.

The advantage of measurements with diffuse reflection is that inhomogeneities of the sample material, e.g. turbidities, do not interfere with the evaluation, but instead support the diffuse reflection.

As opposed to these carriers, which are suitable for reflectance measurements, it is also possible to advantageously use carriers for transmittance measurements which allow incident radiation to pass through. Again, a difference is made between carriers with a smooth and with a rough surface. Said carriers can be made, for example, of plastics, such as polycarbonate, polyethylene or polymethylmethacrylate, which allow infrared radiation in large wave number ranges to pass through. These carriers for transmittance measurement can also have recesses to hold the sample liquids as do the carriers used for reflectance measurement.

In a particularly preferred embodiment, the carrier has one or several openings in which the sample liquid can be placed. Suitable embodiments of carriers with openings include eyes, nets and perforated foils. The sample is applied above the opening of the carriers such that it spreads out. With an appropriate cross section of the opening given, the sample liquid first forms a hanging droplet which covers the opening of the sample carrier. Once dried, a thin hanging film is formed. Particularly suitable diameters of the opening range between 200 and 1000 μm. The stability of the films can be further increased by adding so-called film formers. Film formers include proteins, acrylates and surface-active substances. Sample liquids with a relatively high protein contents, such as whole blood, serum, and plasma usually form films without requiring the addition of film bildners, provided the above cross sections of the openings are given.

The sample liquid can be dried in the same manner as samples are dried on reflecting carriers. The cross section of the opening of the carrier and, if necessary, the addition of the film formers must be adjusted to the sample liquid such that the liquid film which is formed above the opening of the carrier does not rip during drying.

When an infrared spectrum is to be generated, the dried film is exposed to radiation in a direction which is perpendicular to its surface, such that there is no carrier material in the light path. As experience has shown that there is always some sample material adhering to the walls of the carrier, a part of the sample liquid escapes evaluation. To keep this percentage as low as possible, the carrier material can be selected such that it offers as little surface as possible to which liquid can adhere. Perforated foils, for example, can be selected to be as thin as possible so that the edge facing the opening is also as small as possible. Another possibility of reducing the adhesion of sample liquids is to use hydrophobic carrier materials. A perforated foil can be made, for example, of Teflon®, polyethylene, or polypropylene. Particularly suitable metal foils or metal compound foils are those which are coated on both sides with a hydrophobic material such as the above listed plastics. When metal eyes are used, they can be coated with a liquid-repellent material such as Teflon® spray prior to use. Suitable carriers are described in U.S. Pat. No. 5,290,705, the complete contents of which is herewith incorporated by reference.

As only a part of the sample material is exposed to radiation when hanging films are used in transmittance measurement, an integral evaluation corresponding to the preferred method described in P 43 31 596.8 with reflecting carriers is not possible. For a quantitative or semi-quantitative evaluation, it is therefore advantageous to mix a reference substance into the sample material. If the amount of reference substance and the amount of sample materials before the mixing are known, the concentration of the reference substance in the mixture can be calculated. Using an infrared spectrum, the amount of sample material can be concluded based on the absorption of reference substance. It is thus possible to determine the concentration of substance in the sample.

In another advantageous method for quantitative measurement, the thickness of the film is determined interferometrically. The surface of the film which the infrared beam traverses is known because of the light path. The amount of sample material to be evaluated can be concluded from the thickness of the film and the surface exposed to radiation. It is thus possible to quantify the substances in the sample.

Another important characteristic feature of the present invention is to dry the sample on the carrier, which allows eliminating the highly interfering spectrum of water as best as possible. Experience has surprisingly shown that this drying does usually not affect the sample so as to render an analysis and classification impossible. Rather, the drying is an important step to maintain the necessary high reproducibility when the spectra are generated.

The samples can be dried either by simply evaporating the liquid at room temperature or under particular conditions, for example, by creating a vacuum, heating up the sample or storing the sample in the presence of a drying agent. The drying procedure does usually not lead to an absolutely dry sample, but rather leaves a minor percentage of moisture in the sample. An advantage of this procedure is that the sample forms one coherent film where cracks, which could interfere with the evaluation, do not occur.

Depending on the drying conditions, the carrier, and the type of sample used and the drying of the sample leads to a dried remainder of a varying shape in size. When, for example, serum samples are dried on coherent surfaces, a circular enlargement is usually formed where thickness decreases towards the center of the circle. When hanging films are used, an enlargement is formed at the edges toward the carrier material. At the center of the opening, this enlargement changes into a film of a relative uniform thickness.

When the sample is exposed to radiation which is reflected, it is preferred that the entire sample be exposed to IR rays. Based on this integral exposure to radiation, the measurement is largely independent of the drying profile of the sample. This is another essential factor which increases reproducibility of the spectrum evaluation.

In order to generate an infrared spectrum, a sample is exposed to infrared radiation. This infrared radiation may cover the entire infrared range, i.e. a wave number range from 400–15000. When the above mentioned drying method is applied, it is particularly advantageous to use an IR spectroscopy in a wave number range 400–4000 as it exhibits a high specificity.

Any radiation which traverses the sample or is reflected by the sample is received by a detector. To optimize the intensity, one attempts to collect a largest possible part of the radiation. Prior art knows infrared-sensitive detectors, such as bolometer, thermoelements, photovoltaic elements, and semi conductor detectors. Before the beams reach the detector, they can be guided through a system of lenses, diaphragms, and mirrors.

The generation of infrared spectra is sufficiently known in prior art. With respect to the generation of IR spectra of dried samples, please refer to German Patent Application P 43 31596.8.

In conventional methods of evaluating spectra, the transmitted or reflected radiation is measured in dependency upon the wave number. In accordance with the invention, such a spectrum is evaluated by using a procedure with class assignment. To carry out this evaluation process, the spectrum must be digitalized unless a digital recording has been used. This means the spectrum must be converted into a value table containing the absorption or transmittance for discrete wave numbers. The number of value pairs essentially depends upon the capacity of the soft- or hardware used. In accordance with the invention, it is not necessary to isolate individual bands of the spectrum for separate analysis and evaluation. However, for some analyses it has proven to be advantageous if the value table for the evaluation is limited to certain wave number ranges. It is thus possible to select relevant spectrum ranges and to eliminate those parts of the spectrum which contain less important information.

The digitalized spectrum is transferred to a multivariate evaluation procedure which is available as a computer program.

In the invention, multivariate evaluation procedures are understood to be discriminant analyses, regularized discriminant analyses, neuronal networks, cluster analyses, and so forth. The corresponding software packages can be obtained by STSC, STAT SOFT, SAS and Galactic Industries.

Prior to their application in accordance with the invention, the multivariate evaluation procedures must be trained to match the field of application. This is usually done by a number of training runs where the infrared spectra of several samples of known classifications are entered into the evaluation procedure. The evaluation procedure is also provided with the type of classification of individual samples. In such a training run, the evaluation algorithm individually selects parameters ensuring a reliable assignment of the samples to the given classes. The so obtained parameters are used to classify unknown samples in later runs. If a sample of an unknown classification is evaluated and assigned to a class as described above, the evaluation procedure uses an output unit to inform the user which classification has been selected.

A particularly important field of application of the described classification procedure is the assignment of body fluids to clinically relevant groups. The classification procedure can also be advantageously used to classify samples of cell/bacteria suspensions.

A multivariate evaluation procedure usually has a multitude of different classes. With the method of the invention it is, hence, possible to classify a sample where currently known methods require several separate analysis procedures. Classes which belong to internal diseases, for example, are particularly important for clinical analyses. With the method of the invention it is, for example, possible to provide a classification in order to predict whether a liver disease or a renal disease is present. However, the described classification does not replace a clear diagnosis as the spectral changes of the sample may be caused by different diseases or interferences. The known classification is rather a procedure to decide for which disease the samples should be screened with classical methods. It is thus possible to save numerous analytical tests in a clinical laboratory which normally would have been necessary during the admission check.

The invention also comprises a device for classifying samples with a sample carrier, an infrared radiation source to expose a sample on the sample carrier to radiation, a detector for detecting radiation that has been reflected by the sample or has traversed the sample, a storage unit in which output signals of the detector are stored in the form of a spectrum, an evaluation unit in which the spectrum of the sample is subject to a multivariate evaluation procedure and where the sample is assigned to a class based upon a comparison with spectra of a reference sample of a known classification, a display, where the assignment of a sample to be analyzed to a class is graphically or alpha-numerically represented.

The device for classifying samples comprises a sample carrier onto which the sample to be analyzed is placed. A sample carrier in accordance with the invention must be resistant to the sample, as it is the site on which the drying of the sample occurs. It is particularly advantageous to use sample carriers which have a recess on their surface into which the sample can be placed. In addition to sample carriers with a diffusely reflecting surface, it is also possible to employ surfaces with specular reflection. When a diffusely reflecting carrier is used, primarily diffusely reflected radiation is evaluated, while specularly reflected radiation is excluded. When a sample carrier with a specular reflection is used, the directly reflected radiation is also evaluated.

Arrangements for evaluating diffuse or direct reflection are known in prior art and are not further explained at this point. An arrangement for evaluating diffusely reflected radiation is explained in greater detail in German Patent Application P 43 31596.8.

In order to generate an infrared spectrum, the sample is exposed to infrared radiation on the sample carrier. Infrared radiation in the above described wave number ranges can be generated with commercially available IR spectrometers manufactured by Nicolet, Bruker, and Perkin-Elmer, for example.

Principally, a spectrum can be generated in two different ways. In the first procedure, a very small wave number range is filtered out of the continuous radiation of the radiation source and used to expose the sample. In the second principle, the sample is exposed to radiation with a continuous spectrum and the light which is reflected by the sample or traverses the sample is analyzed in dependency upon the wave number. Recently, Fourier transform spectroscopy has prevailed on the market to generate infrared spectra. Grid or prism systems can also be used, but today are of minor importance.

The transmitted or reflected light measured in accordance with one of the principles is stored in a conventional storage element, e.g. a RAM, in dependency upon its wave number.

Prior to the evaluation, the transmittance or reflection spectrum of the sample can be subject to a great number of modifications. If contaminations or interfering substances are known to be contained in the sample, the spectrum thereof can be subtracted from the generated spectrum. Depending on the instrument employed, it is possible to carry out further adjustments to compensate wave-number-dependent differences in the sensitivity of the instrument. A number of modifications to which a spectrum can be subject are described in European Patent Application EP-A-0 584 931.

A central aspect of the invention proposes to evaluate the spectrum of the sample by means of a multivariate evaluation procedure. The basis of multivariate evaluation procedures is to train them using samples of known classifications. This means that first infrared spectra generated according to identical or at least comparable measuring procedures were generated for a great number of samples. These spectra are supplied to the multivariate evaluation procedure and the evaluation procedure is always informed to which class the respective spectrum is assigned. In a great number of evaluation procedures (discriminant analysis, cluster analysis), a correlation matrix is first generated. Based on the correlation matrix, the evaluation procedure first determines which wavelengths to use with which classification influence. The wavelengths used for the evaluation generate a space whose dimensions are identical with the number of wavelengths. The evaluation procedure selects a subspace where the samples are assigned to classes in a largely unique manner. The assignment of samples to a class is a result of their spatial proximity to said subspace.

The assignment of an unknown sample to a class can be represented in a display or on paper, for example. In many cases, a graphic representation is preferred to a merely numerical assignment as it is easier for the reader to determine how clearly a sample can be assigned to a certain class.

As opposed to prior art, the invention allows a more exact and reproducible classification of body fluid. Moreover, with the invention, it is also possible to analyze and classify more complex body fluids. Another advantage is that the device in accordance with the invention allows the use of relatively inexpensive sample carriers. The use of disposable sample carriers has the advantage of avoiding carry-over problems, thus allowing a more hygienic analysis. Yet another advantage of the invention is that it requires only a few microliters of sample for the analysis.

The following examples and figures are intended to further specify the method in accordance with the invention.

FIG. 1: Device for classifying clinically relevant liquids and suspensions

FIG. 2: Flow chart showing the classification procedure

Figure 3A:
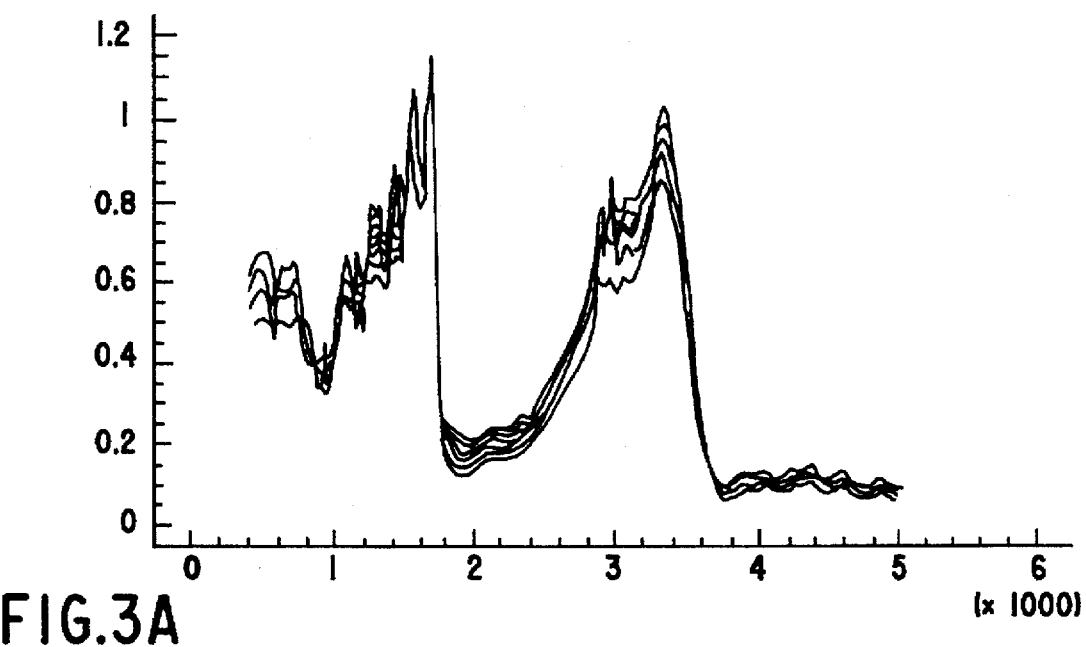
Figure 3B:
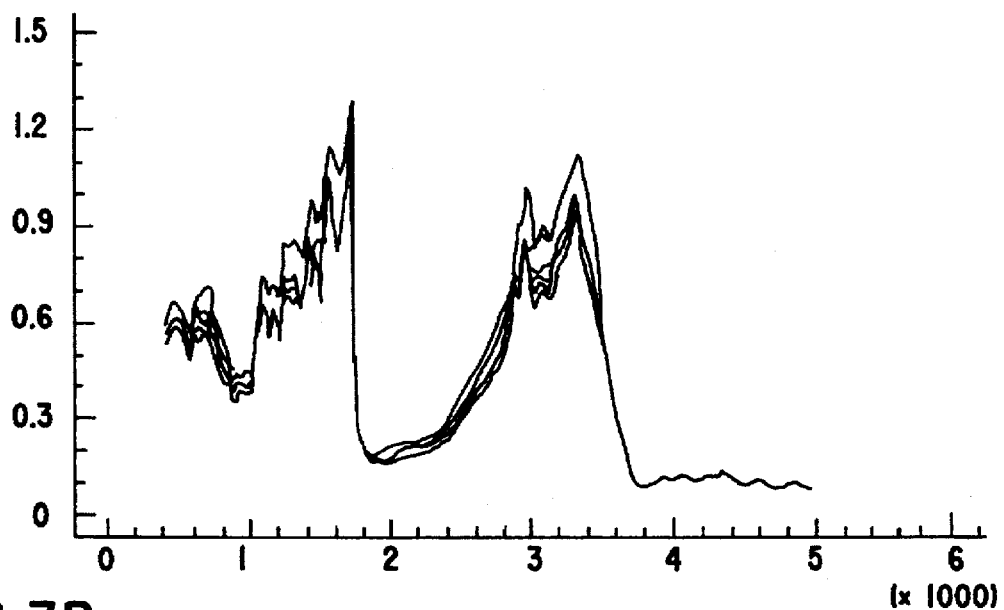
Figure 3C:
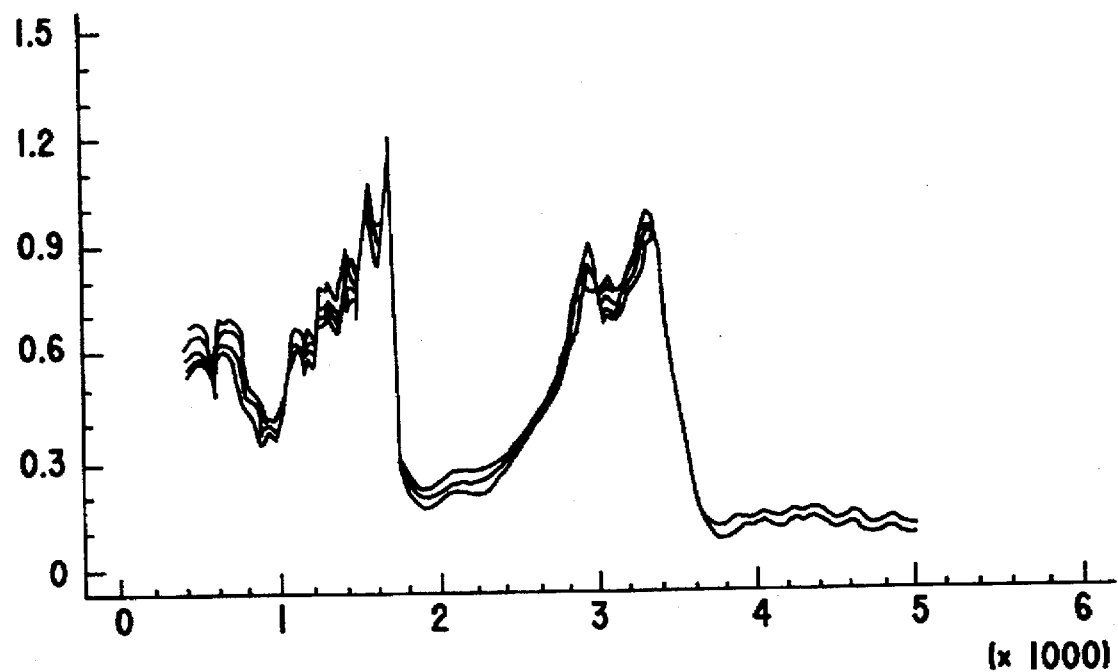

FIG. 3(A–C): Spectra of serum samples

Figure 4:
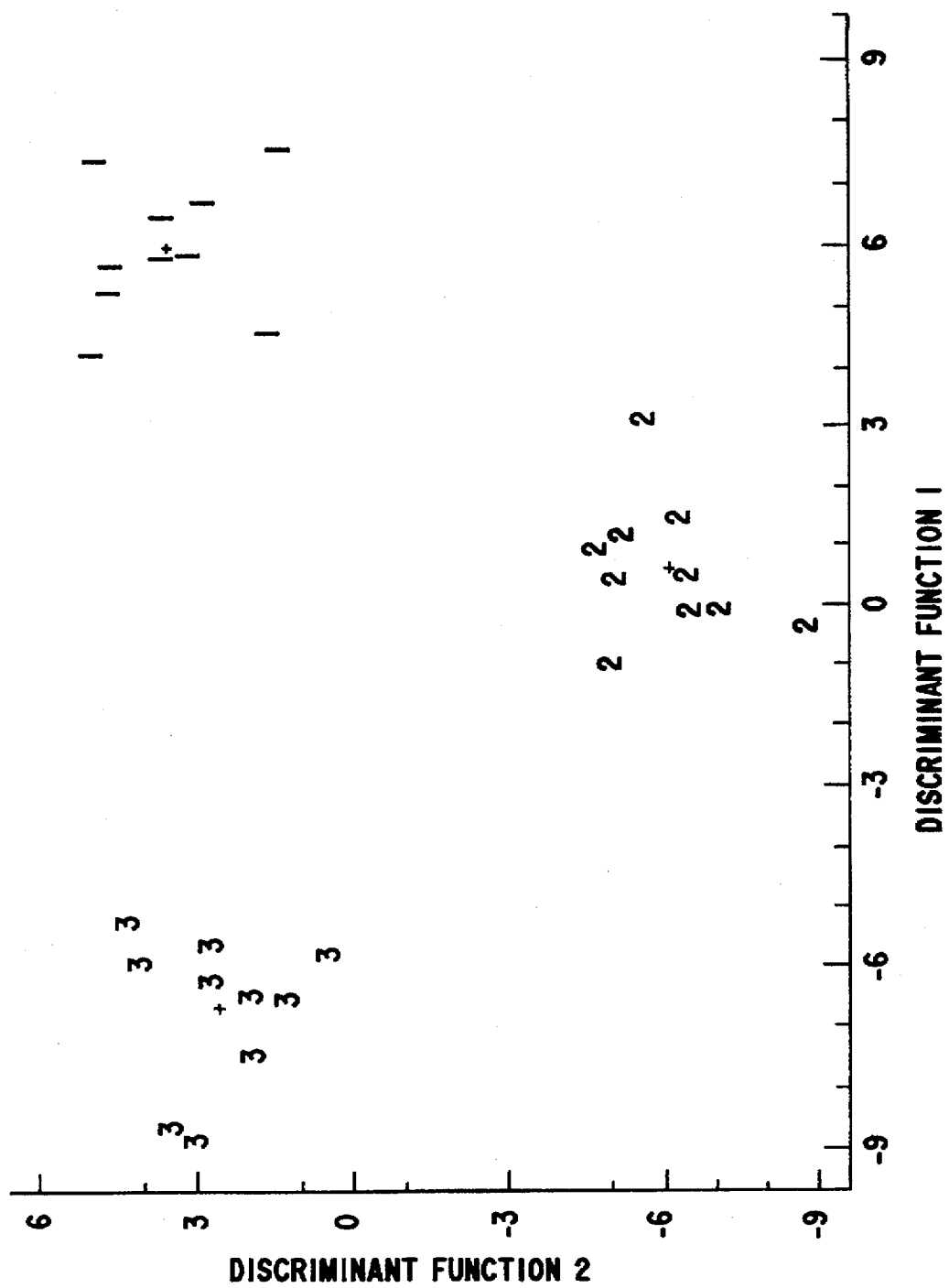

FIG. 4: Result of a discriminant analysis of the spectra of FIG. 3

Figure 5:
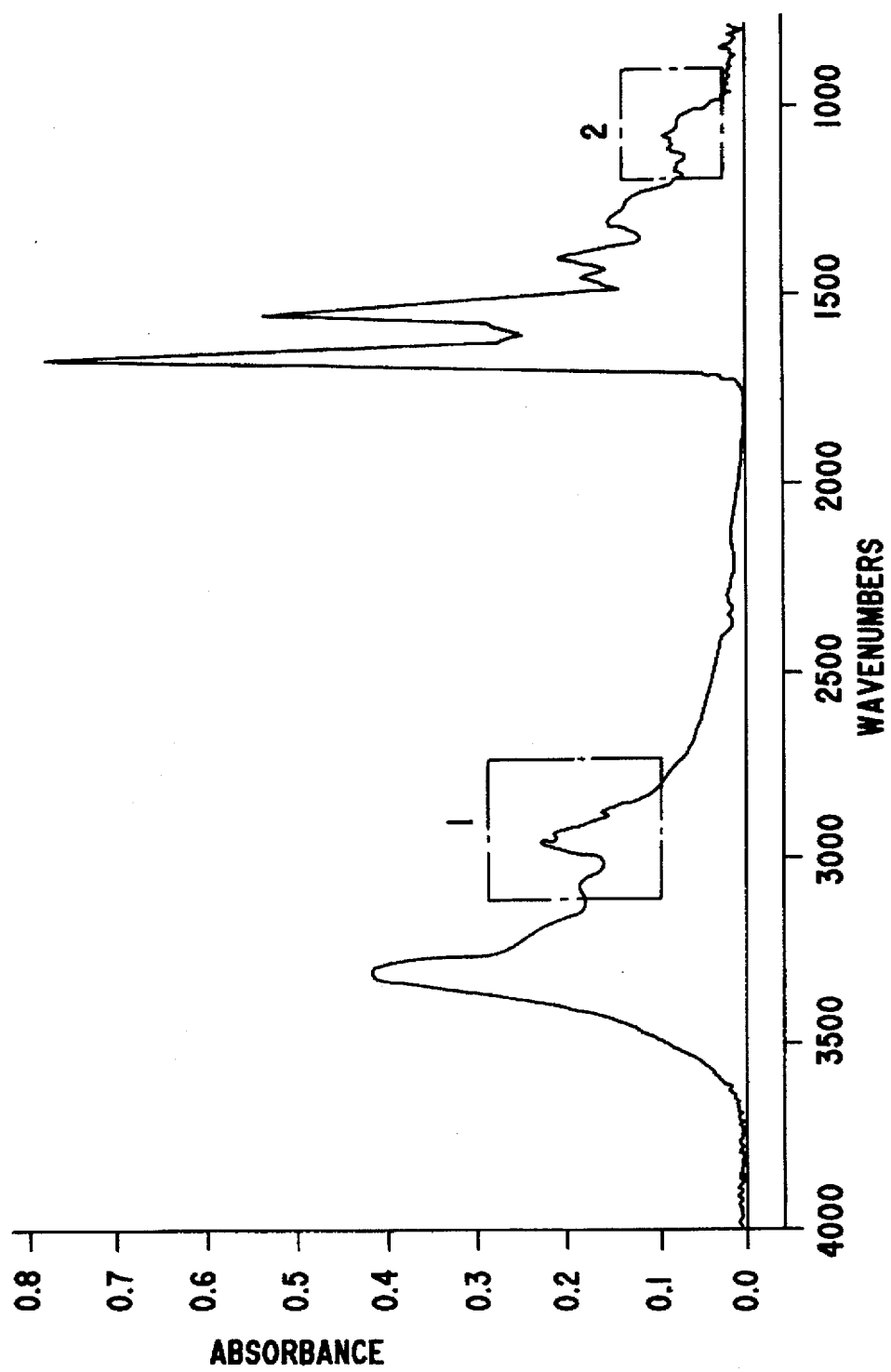

FIG. 5: Selection of wavelength ranges for a discriminant analysis

Figure 6:
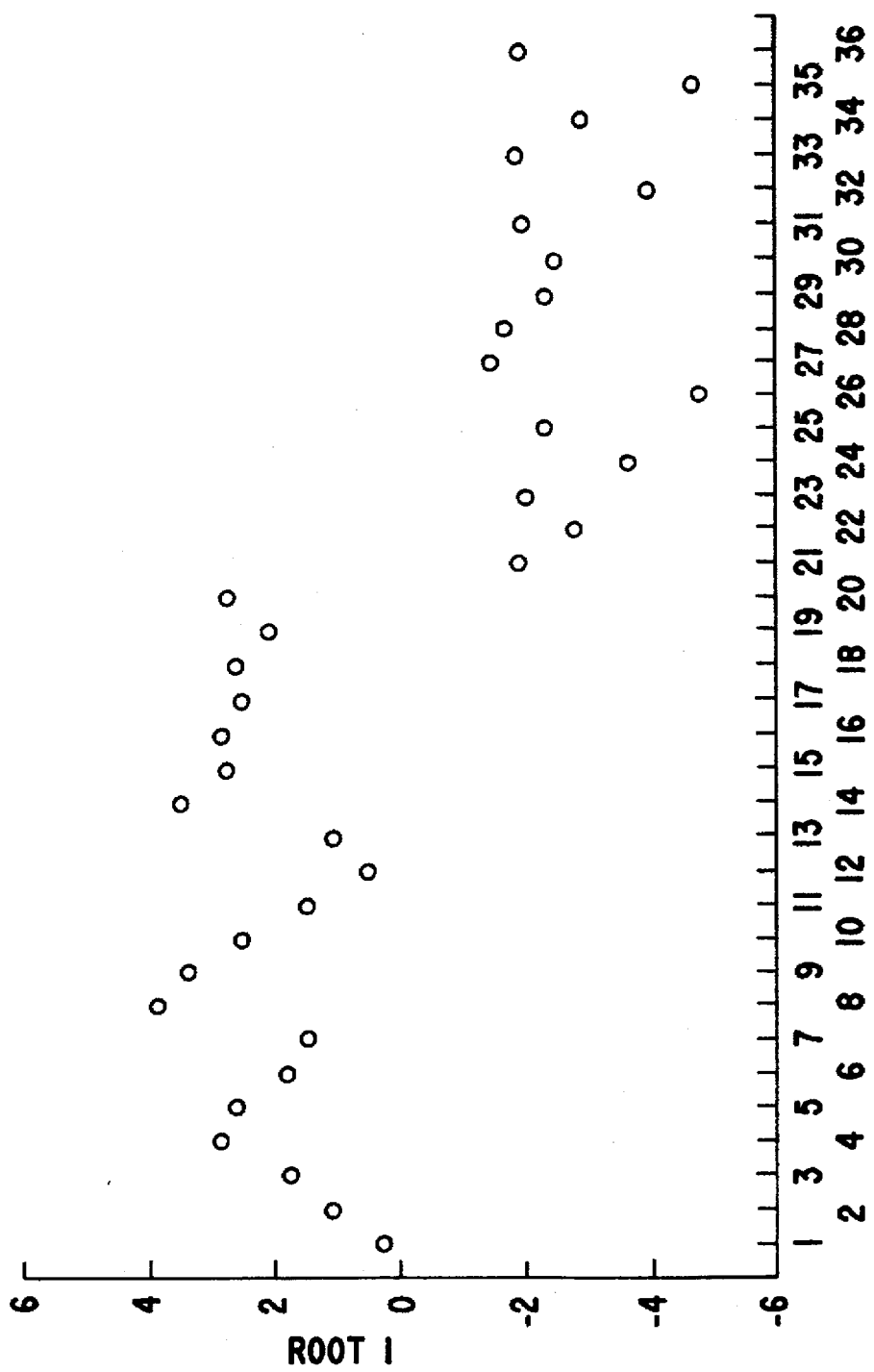

FIG. 6: Result of a discriminant analysis of serum samples of diabetics

Figure 7:
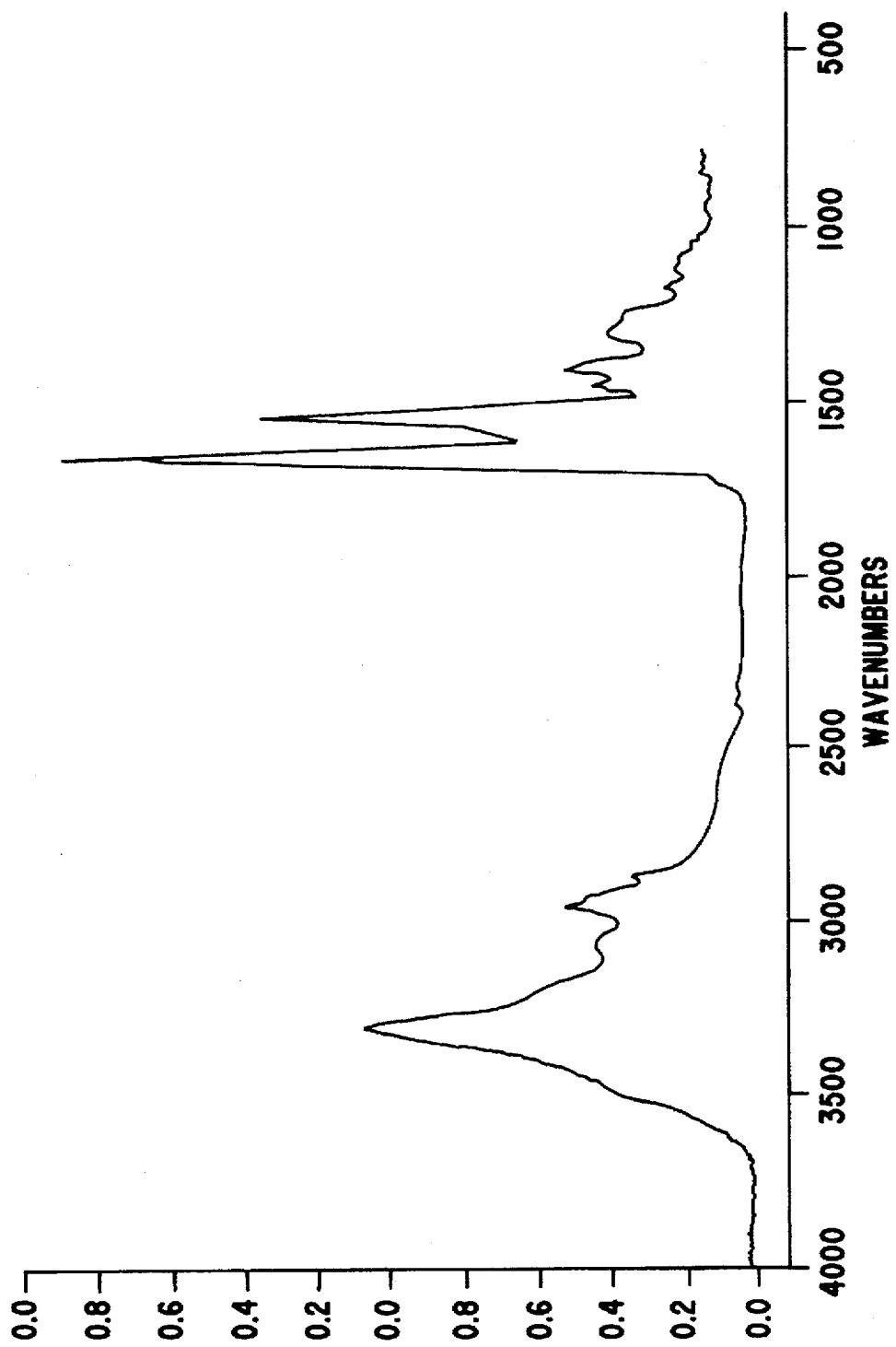

FIG. 7: Transmittance spectrum, generated on a hanging film

Figure 8:
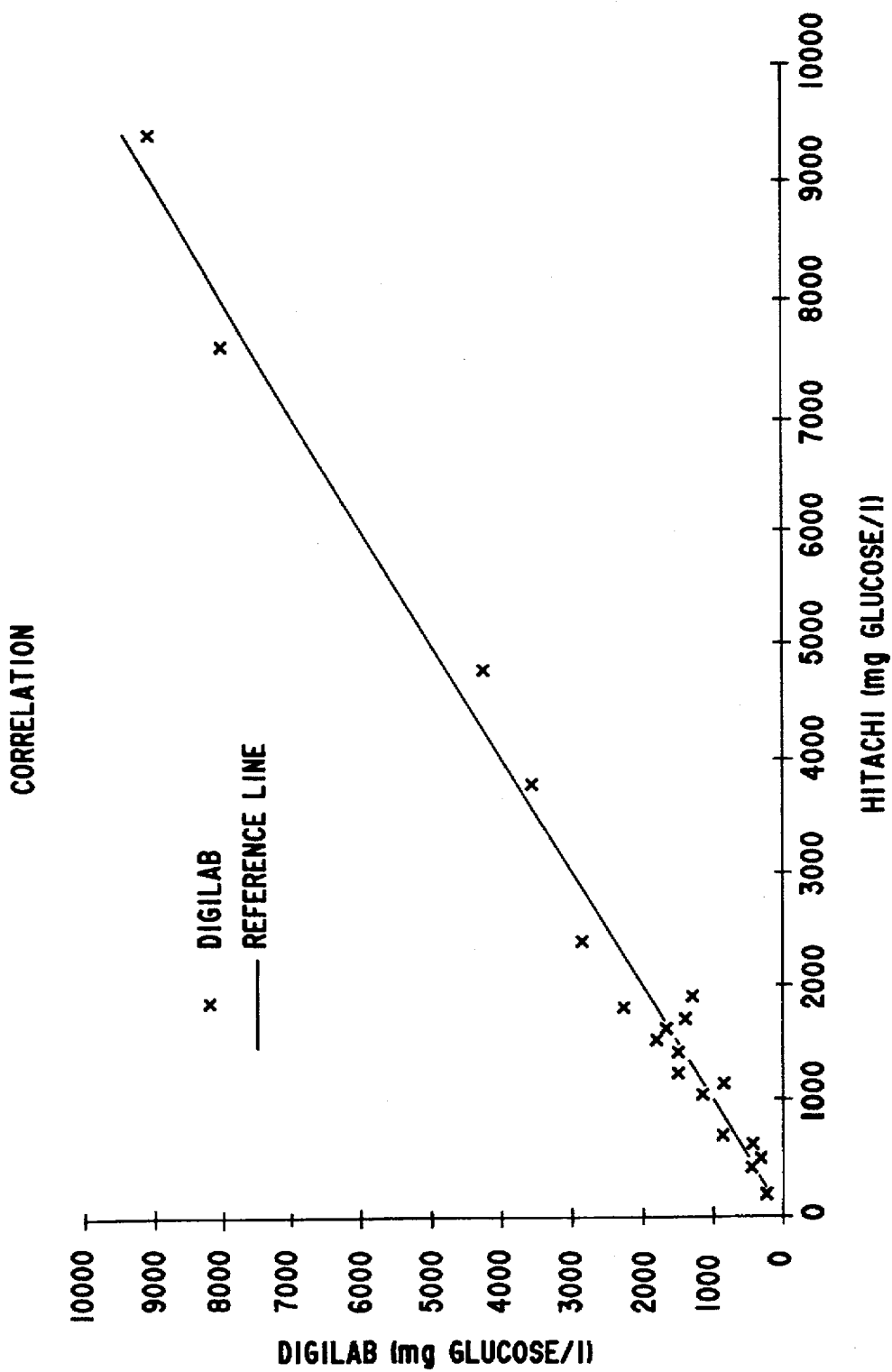

FIG. 8: Method comparison

Figure 9:
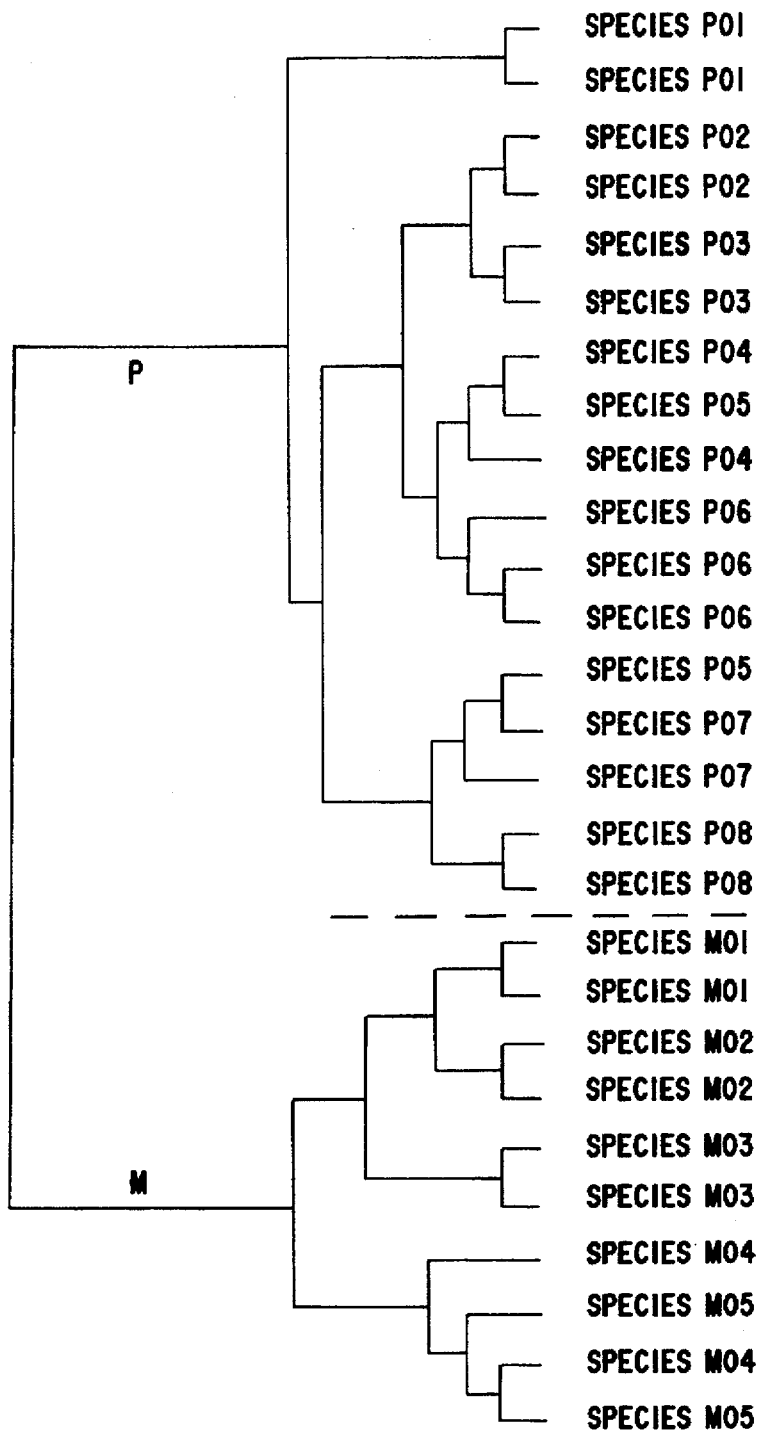

FIG. 9: Classification of suspensions of bacteria

FIG. 1 is a sketch of the device in accordance with the invention for classifying clinically relevant liquids and suspensions.

The dried sample (1) is placed into the recess of a sample carrier (2). The sample carrier is a brass plate whose surface is coated with gold. Radiation emitted by the radiation source (3) exits through an aperture in the concave mirror (4) and reaches sample (1). The beams illuminate the sample in its entirety. Radiation which is diffusely reflected by sample (1) and sample carrier (2) is collected by the concave mirror (4) and focused on detector (5). The analog signals of the detector are converted into digital signals in an analog-to-digital converter (A/D). These digital signals are transferred to a microprocessor (CPU) to which the storage unit is connected (RAM). An algorithm for a discriminant analysis (DA) is either provided on a separate information carrier, e.g. a hard disk or a floppy disk, or stored in an internal storage element (RAM). The generated spectra are evaluated in a discriminant analysis procedure and the results are represented on an output medium (OUT), e.g. a screen or plotter.

FIG. 2 is a flow diagram showing the relation of the calibrator of the evaluation procedure and the analysis of unknown samples. To carry out the calibration, infrared spectra of samples of known classes are first generated. They are used to establish a calibration model which means that parameters are selected for the evaluation procedure to correctly assign the samples. When unknown samples are analyzed, the infrared spectra thereof are evaluated based upon the selected parameters and, if possible, assigned to the known classes of the evaluation procedure.

EXAMPLE 1

Assigning samples to the following classes: "renal insufficiency", "normal", "cirrhosis of the liver".

FIGS. 3(A–C) show spectra of samples in a wave number range of 400 to 5000. The spectra were obtained by applying 1 to 2 µl of serum onto sample carriers, which had a gold-plated surface with a roughness of less than µm. The samples were stored under ambient conditions which caused the samples to dry within about 20 minutes. The reflection spectra of the samples were integrally measured with an infrared spectrometer manufactured by Bruker. In this context, integral measurement means that the sample on the carrier is in its entirety exposed to the radiation.

With the naked eye it is hardly possible to detect differences in the spectra shown in FIGS. 3(A–C). Neither an analysis of the main components nor a factor analysis could provide a satisfactory classification of the samples. Using regularized discriminant analysis, however, the samples could be clearly assigned to classes. The algorithm employed was a discriminant analysis algorithm according to J. H. Friedmann in "Journal of the American Statistical Association, Vol. 84, No. 405 (1989), Theory and Methods". A corresponding FORTRAN source code can be obtained from J. H. Friedmann upon request. The discriminant analysis procedure was trained by making the respective sample classes available to the algorithm.

The method was validated according to the leave-one-out method. In this procedure, n-1 samples are used to condition the discriminant analysis procedure for one set of n analysis samples. It was checked if the n-th sample was assigned to the correct class. This procedure was cyclically repeated for all samples.

FIG. 4 is a two-dimensional representation of the results of this discriminant analysis. The spectra shown in FIG. 3(A–C) were made available to the discriminant analysis by storing 23 value pairs of wave numbers and intensities for each spectrum. The spectra were reduced to 23 value pairs by equidistantly using one value pair for each 100 wave numbers. In FIG. 4 it can be clearly seen that samples of the same class (class 1: renal insufficiency; class 2: normal samples; class 3: cirrhosis of the liver) can be found in the same area of the two-dimensional representation. This means that the sample of an unknown classification can be clearly assigned to a class by means of discriminant analysis.

EXAMPLE 2

Assigning samples to the following classes: type I or type II diabetes.

36 serum samples of patients with type I or type II diabetes were collected and approximately 2 µl of each sample were applied onto a gold-plated sample carrier with a rough surface. Once the serum samples were dried under normal ambient conditions, reflection spectra were generated with an infrared spectral analyzer manufactured by Bruker. The spectra were subject to data reduction by selecting the spectral ranges 1 and 2 as shown in FIG. 5. In ranges 1 and 2, value pairs consisting of wave number and intensity were generated at intervals of 4 $cm^{-1}$ and subject to a discriminant analysis. FIG. 6 shows a two-dimensional representation of the results of a discriminant analysis. The X-axis shows the numbering of the samples, with samples 1 to 20 being samples of type I diabetics and samples 21 to 36 being samples of type II diabetics. One can see that both types of the disease are clearly separated in the direction of the Y-axis. While samples of diabetics of type I are found in the range between 0 and +4, those of type II diabetics show Y-values between −1 and −5.

EXAMPLE 3

Transmittance spectrum with samples on a plastic net

3 µl of protein solution were pipetted into the mesh of a woven plastic net (Fluortex, manufactured by Schweizer Seidengazefabrik AG Thal) with a mesh diameter of 850 µm so that the droplet wetted all edges of a mesh of the net, while it was freely hanging. After drying, the transparent film was analyzed by measuring the transmittance with an IR microscope manufactured by Digilab. FIG. 7 shows the generated transmittance spectrum. FIG. 8 contains the corresponding calibration for glucose in a 5% bovine serum albumin solution. The abscissa shows the reference measurements obtained with a Hitachi 704 analyzer, whereas the ordinate shows the corresponding results obtained with a Digilab instrument based on a partial-least-squares evaluation.

EXAMPLE 4
Classification of bacteria suspensions

FIG. 9 shows a classification of samples containing different species of pseudomonas and micrococci bacteria. The classification is obtained by applying 2 µl of bacteria suspension which contain $10^6$ to $10^7$ bacteria on a gold-plated carrier with a roughness of less than 1 µm. Once the samples were dried under normal ambient conditions, infrared spectra with wave number ranging between 800 and 1200 were generated. Of each sample, at least two randomized spectra were generated.

Cluster analysis was employed to clearly distinguish the two types of bacteria from one another. In the figure, this fact is represented in that there is no assignment between the p species (pseudomonas) and the m species (micrococci). The broken line in FIG. 9 shows that the separation of p and m species is already possible on a very simple level of the cluster analysis. Moreover, it was also shown that almost all double determinations were correctly assigned to one another.

This indicates that the method of the invention is capable of distinguishing even bacteria species of the same kind, but having a different previous history.

List of reference numerals
- (1) sample
- (2) sample carrier
- (3) source of radiation
- (4) concave mirror
- (5) detector
- (A/D) analog-to-digital converter
- (CPU) microprocessor
- (RAM) storage element
- (DA) discriminant analysis
- (OUT) output medium

We claim:

1. A method of analyzing clinically relevant liquids and/or suspensions, comprising
   a) measuring the infrared spectra of a plurality of samples belonging to known classes,
   b) implementing a multivariate evaluation procedure and training the multivariate evaluation procedure by selecting parameters ensuring a reliable assignment of the samples to the known classes,
   c) storing the parameters of the multivariate evaluation procedures obtained,
   d) providing a sample of the liquid and/or suspension to be analyzed,
   e) applying the sample to a carrier,
   f) drying the sample,
   g) exposing the sample to infrared radiation,
   h) generating an infrared spectrum of the sample,
   i) analyzing the infrared spectrum by means of a multivariate evaluation procedure, and
   j) assigning the sample to a class of the multivariate evaluation procedure.

2. Method of claim 1, wherein the carrier reflects infrared radiation to generate a reflection spectrum of the sample.

3. Method of claim 2 wherein the reflection spectrum is a diffuse reflection spectrum.

4. Method of claim 1, wherein the liquids and/or suspensions which are analyzed are body fluids which are whole blood, hemolysate, serum and/or plasma.

5. Method of claim 1, wherein a suspension of cell and/or bacteria is analyzed.

6. Method of claim 2, wherein in step (g), the entire sample is irradiated with the infrared radiation.

7. Method of claim 1, wherein steps (a), (b), and (c) are carried out one or more times while steps (d) to (j) are carried out in multiples and cyclically using different samples.

8. Method of claim 1, wherein the multivariate evaluation procedure is a discriminant analysis, a neuronal net, or a cluster analysis.

9. Method of claim 8, wherein the discriminant analysis is a regularized discriminant analysis.

10. Method of claim 1, wherein infrared spectrum ranging from 400 to 15000 $cm^{-1}$ are generated.

11. Method of claim 10, wherein infrared spectrum ranging from 400 to 4000 $cm^{-1}$ are generated.

12. Method of claim 1, wherein the samples of known classification are samples from which it is known that an internal disease is present.

13. Method of claim 1, wherein the samples of known classification are samples from which it is known that a liver or renal disease is present.

14. Method of claim 1, wherein the samples of known classification are samples of patients with type I or type II diabetes.

15. Method of claim 1, wherein additionally at least one sample is used which is a sample of a healthy patient.

16. Method of analyzing clinically relevant liquids and/or suspensions, comprising
   a) providing a sample of the liquid and/or suspension,
   b) placing the sample onto a carrier having at least one opening in which the sample forms a hanging film,
   c) drying the sample,
   d) allowing radiation to traverse the dried sample contained in the opening,
   e) detecting radiation transmitted across the dried sample to generate an infrared spectrum,
   f) evaluating the infrared spectrum to determine the concentration of at least one analyte contained in the sample, and/or to classify the sample.

17. Method of claim 16, wherein the at least one opening has a diameter of 200 to 1000 µm.

18. Method of claim 16, wherein the carrier is an eye, a net or a perforated foil.

19. Method of claim 16, wherein a defined quantity of a reference substance is added to the sample, and the amount of the sample material detected by the infrared beam is determined from the absorption of the reference substance.

20. Method of claim 16, wherein the thickness of the suspended film is interferometrically determined, and the thickness of the film is used to determine the amount of sample detected by the infrared beam.

21. Method of claim 16, wherein film-forming substances are added to the sample liquid to increase the stability of the hanging film.

22. Method of claim 16, wherein the infrared spectrum obtained in step (e) is analyzed by means of a multivariate evaluation procedure.

23. Method of claim 22, wherein the multivariate evaluation procedure is a discriminant analysis, a neuronal net, or a cluster analysis.

24. Method of claim 23, wherein the discriminant analysis is a regularized discriminant analysis.

25. Method of claim 16, wherein infrared spectrum ranging from 400 to 15000 $cm^{-1}$ are generated.

26. Method of claim 25, wherein infrared spectrum ranging from 400 to 4000 $cm^{-1}$ are generated.

27. Method of claim 16, wherein cell/bacteria suspensions are used as the samples.

* * * * *